(12) United States Patent
Hyde et al.

(10) Patent No.: US 9,314,523 B2
(45) Date of Patent: Apr. 19, 2016

(54) INGESTIBLE SALT GRABBER

(75) Inventors: Roderick A. Hyde, Redmond, WA (US); Wayne R. Kindsvogel, Seattle, WA (US); Gary L. McKnight, Bothell, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 733 days.

(21) Appl. No.: 12/924,212

(22) Filed: Sep. 21, 2010

(65) Prior Publication Data

US 2012/0070380 A1    Mar. 22, 2012

(51) Int. Cl.
*A61K 9/22* (2006.01)
*A61K 41/00* (2006.01)
*A61M 31/00* (2006.01)
*A61K 31/74* (2006.01)

(52) U.S. Cl.
CPC .............. *A61K 41/0028* (2013.01); *A61K 31/74* (2013.01); *A61M 31/002* (2013.01)

(58) Field of Classification Search
CPC ..... A61K 9/50; A61K 9/5005; A61K 9/5073; A61M 31/002; A61M 35/00
USPC ............................... 424/464–489; 604/890.1
See application file for complete search history.

(56) References Cited

U.S. PATENT DOCUMENTS

| | | | | |
|---|---|---|---|---|
| 5,297,607 | A * | 3/1994 | Beauchamp | 160/84.04 |
| 6,063,404 | A * | 5/2000 | Timpe | A61K 9/006 424/435 |
| 6,123,861 | A | 9/2000 | Santini, Jr. et al. | |
| 7,556,799 | B2 | 7/2009 | Charmot et al. | |
| 7,651,858 | B2 | 1/2010 | Bakker et al. | |
| 2005/0220750 | A1 * | 10/2005 | Robert | A61K 31/74 424/78.1 |
| 2008/0125394 | A1 | 5/2008 | Savica | |
| 2008/0188837 | A1 * | 8/2008 | Belsky | A61K 9/0053 604/890.1 |
| 2008/0233073 | A1 | 9/2008 | Charmot et al. | |
| 2008/0241092 | A1 | 10/2008 | Charmot et al. | |
| 2008/0241093 | A1 | 10/2008 | Charmot et al. | |
| 2008/0260679 | A1 | 10/2008 | Charmot et al. | |
| 2008/0262285 | A1 | 10/2008 | Black et al. | |
| 2009/0148533 | A1 | 6/2009 | Charmot et al. | |
| 2009/0155370 | A1 | 6/2009 | Cope et al. | |
| 2009/0186093 | A1 * | 7/2009 | Liu | A61K 9/5026 424/497 |
| 2010/0104527 | A1 | 4/2010 | Mansky et al. | |
| 2010/0111891 | A1 | 5/2010 | Albrecht et al. | |
| 2010/0111892 | A1 | 5/2010 | Chang et al. | |

FOREIGN PATENT DOCUMENTS

WO    WO 2008/012725 A2    1/2008
WO    WO 2008012725 A2 *  1/2008  ............ A61M 37/00

OTHER PUBLICATIONS

Liu et al , Magnetic-sensitive Behaviour of Intelligent Ferrogels for Controlled Release of Drug, 2006, Langmuir, 22, 5974-5978.*
Lui et al (Magnetic-sensitive behavior of intelligent ferrogels for controlled release of drug, Langmuir, 2006, 22, 5975-5978).*
Liu et al (Magnetic-sensitive behavior of intelligent ferrogels for controlled release of a drug, Langmuir, 2006, 22, 5975-5978).*
Liu et al (Magnetic-sensitive behavior of intelligent ferrogels for controlled release of a drug, Langmuir 2006, 22, 5975-5978).*
Ahmed et al.; "Bioadhesive microdevices with multiple reservoirs: a new platform for oral drug delivery"; Journal of Controlled Release ; 2002; pp. 291-306; vol. 81; Elsevier Science B.V.
Angelos et al.; "pH-Responsive Supramolecular Nanovalves Based on Cucurbit[6]uril Pseudorotaxanes"; Angew. Chem. Int. Ed.; 2008; pp. 2222-2226; vol. 47; Wiley-VCH Verlag GmbH & Co. KGgA, Weinheim.
Craciunescu et al.; "Synthesis, characterization and drug delivery application of the temperature responsive pNIPA hydrogel"; Journal of Physics: Conference Series; 2009; pp. 1-4; Vo. 182; IOP Publishing Ltd.
Danowski et al.; "The Use of Cation Exchange Resins in Clinical Situations"; Ann. Internal Med.; 1951; pp. 529-541; vol. 35, No. 3.
Friedman, I. S.; "Problems of Cation-Exchange-Resin Therapy"; Arch. Intern Med.; 1952; pp. 99-106; vol. 89, No. 1.
Greenman et al.; "Probable Clinical Utility of Cation Exchange Resins"; J. Clin Invest.; Sep. 1951; pp. 1027-1031; vol. 30, No. 9.
Hu et al.; "Nano-ferrosponges for controlled drug release"; Journal of Controlled Release; 2007; pp. 181-189; vol. 121; Elsevier B.V.
Ju et al.; "Biodegradable 'intelligent' materials in response to chemical stimuli for biomedical applications"; Expert Opin. Ther. Patents; 2009; pp. 683-696; vol. 19, No. 5; Informa UK, Ltd.
Liu et al.; "Magnetic-sensitive behavior of intelligent ferrogels for controlled release of drug"; Langmuir; Jul. 4, 2006; Abstract; one page; pp. 5974-5978; vol. 22, No. 14.
Majeti et al.; "Nano and Microparticles as Controlled Drug Delivery Devices"; J Pharm Pharmaceut Sci; 2000; pp. 234-258; vol. 3, No. 2.
McChesney et al.; "Effects of Some Ion Exchange Resins on the Mineral Metabolism of Rats"; Feb. 1950; pp. 264-276; vol. 160.
Miyata et al.; "Biomolecule-sensitive hydrogels"; Advanced Drug Delivery Reviews; 2002; pp. 79-98; vol. 54; Elsevier Science B.V.
Purolite Ion Exchange Resins; Application Guide; Sep. 9, 2008; five pages; located at www.purolite.com.
Ramanujan et al.; "The mechanical behavior of smart magnet-hydrogel composites"; Smart Materials and Structures; 2006; pp. 952-956; vol. 15; IOP Publishing Ltd.
Satarkar et al.; "Magnetic hydrogel nanocomposites for remote controlled pulsatile drug release"; Journal of Controlled Release; 2008; pp. 246-251; vol. 130; Elsevier B.V.

(Continued)

*Primary Examiner* — Michael G Hartley
*Assistant Examiner* — Micah-Paul Young (57) ABSTRACT

Disclosed herein include embodiments related to compositions, devices, computer systems, computer-implemented methods, and computer program products associated with an ingestible salt grabber.

40 Claims, 2 Drawing Sheets

(56) References Cited

OTHER PUBLICATIONS

Sona, P.S.; "Nanoparticulate Drug Delivery Systems for the Treatment of Diabetes"; Digest Journal of Nanomaterials and Biostructures; Apr.-Jun. 2010; pp. 411-418; vol. 5, No. 2.

Spencer et al.; "Cation Exchange in the Gastrointestinal Tract"; British Medical Journal; Mar. 13, 1954; pp. 603-606.

Strauss, Stephen; "Parse the salt, please"; Nature Medicine; Aug. 2010; pp. 841-843 (with correction sheet attached); vol. 16, No. 8; Nature America, Inc.

Tao et al.; "Microfabricated drug delivery systems: from particles to pores"; Advanced Drug Delivery Reviews; 2003; pp. 315-328; vol. 55; Elsevier Science B.V.

Varde et al.; "Microspheres for controlled release drug delivery"; Expert Opin. Biol. Ther.; 2004; pp. 35-51; vol. 4, No. 1; Ashley Publications Ltd.

Vector Laboratories; Chitin Hydrolysate; Product Information Sheet; one page; printed on Jul. 23, 2010; located at www.vectorlabs.com/catalog.aspx.

Zhang et al.; "A Smart Membrane Based on an Antigen-Responsive Hydrogel"; Biotechnology and Bioengineering; Jul. 1, 2007; pp. 976-984; vol. 97, No. 4; Wiley Periodicals, Inc.

* cited by examiner

INGESTIBLE SALT GRABBER

SUMMARY

The present disclosure relates to compositions comprising, for example, a housing including at least one ingestible resin and one or more controllable ports. The present disclosure relates to compositions, among other things, including at least one ingestible resin and one or more cell surface molecules. The present disclosure relates to articles of manufacture including, among other things, an article including a composition having a housing with one or more controllable ports, and at least one ingestible resin. Also included herein are foodstuffs including an ion exchange resin and an ingestible food product. Also disclosed herein are articles of manufacture including an article including a composition having an ingestible resin and one or more cell surface molecules. In an embodiment, a method of modulating at least one ion in a biological tissue includes providing a composition to a biological tissue, the composition including a housing and at least one ingestible resin, and one or more controllable ports.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Living subjects require ions for survival. However, in certain instances a subject may consume or otherwise ingest too much of one or more ions, which can cause detrimental biological consequences. For example, too much sodium has been linked to high blood pressure, obesity, heart attack, stroke, and other health problems in humans. See, for example, Strauss, Nat. Med. Vol. 16, no. 8, pp. 841-843 (2010), which is incorporated herein by reference. In an embodiment disclosed herein, compositions and methods relate to capturing one or more types of ions ingested by a subject. In an embodiment, the compositions and methods relate to retaining the ions for excretion, rather than absorption, by the subject.

In an embodiment, the composition includes a housing including at least one ingestible resin and one or more controllable ports. In an embodiment, the housing includes at least one of a coating, or other enclosure (e.g., capsule, frame, container, device, microchip, silicon wafer, etc.). In an embodiment, the composition includes at least two resins. In an embodiment, the composition includes at least two different resins. In an embodiment, the housing is heterogeneous (e.g., coating on a portion of the composition, and device on a portion of the composition, etc.) In an embodiment, the composition further includes one or more resins located externally to the housing. In an embodiment, the one or more resins located externally to the housing provide an additional binding capacity for the same target ion or a different target ion, of the resin located internal to the housing.

In an embodiment, the composition includes an ion exchange resin including one or more controllable ports. In an embodiment, the resin includes at least one polymer. In an embodiment, the at least one polymer includes at least one of polyester, polylactic acid, polylactic-co-glycolic acid, cellulose, nitrocellulose, urea, urethane, phosphatidylcholine, cholesterol, phosphatidylethanolamine, phospholipid, ganglioside, dioleoylphosphatidylethanolamine, surfactant, polyacid, phthalate, chitin, chitosan, collagen, polyethylene oxide, poly ((β-benzyl-L-aspartate), poly (ε-caprolactone), poly(DL-lactide-co-glycolide), polybutylcyanoacrylate, alginate, poly(adipic anhydride), gelatin, 1,5-dioxepan-2-one, D,L-dilactide, or other polymer. In an embodiment, the at least one polymer includes at least one of polyvinyl acetate phthalate, hydroxypropyl methyl cellulose phthalate, methacrylic acid-methacrylic acid ester copolymers, cellulose acetate trimellitate, carboxymethyl ethylcellulose, hydroxypropyl methylcellulose acetate succinate, cellulose acetate phthalate, poly(methacrylic acid), or other polymer. In an embodiment, the polymer includes polyfluoroacrylic acid (polyFAA). In an embodiment, the polymer includes a crosslinked cation exchange polymer salt and an effective amount of a linear polyol sufficient to stabilize the polymer salt. See, for example U.S. Patent App. Pub. No. 2010/0111891, which is incorporated herein by reference. In an embodiment, the composition further comprises water, for example, in an amount sufficient to reduce or assist in the release of the ion from an ion-loaded exchange resin during storage.

In an embodiment, a linear polyol is added to the composition as a stabilizer for the polymer salt. For example, in an embodiment the linear polyol includes at least one of a linear sugar (i.e., a linear sugar alcohol). In an embodiment, the linear sugar alcohol includes at least one of D-(+) arabitol, erythritol, glycerol, maltitol, D-mannitol, ribitol, D-sorbitol, xylitol, threitol, galactitol, isomalt, iditol, lactitol, and the like, or any combinations thereof. In an embodiment, the linear polyol is present from at least about 1 wt. %, at least about 2 wt. %, at least about 3 wt. %, at least about 4 wt. %, at least about 5 wt. %, at least about 6 wt. %, at least about 7 wt. %, at least about 8 wt. %, at least about 9 wt. %, at least about 10 wt %, at least about 15 wt. %, at least about 20 wt. %, at least about 25 wt. %, at least about 30 wt. %, at least about 35 wt. %, at least about 40 wt. %, at least about 45 wt. %, at least about 50 wt. %, at least about 55 wt. %, at least about 60 wt. %, or any amount therebetween or greater.

In an embodiment, the ion exchange resin is loaded with an ion (e.g., hydrogen, ammonium, lithium, etc.) that is displaced (often referred to as "exchanged") upon binding of another ion (e.g., the target ion) from the biological tissue. See, e.g., Friedman, "Problems of Cation-Exchange-Resin Therapy," available online. See for example, the worldwide web at archinternmed.com, last visited on Apr. 13, 2010, the contents of which are incorporated herein by reference.

For example, certain polymers include particular desirable characteristics for use with the resin or housing, including: poly(urethanes) for elasticity; poly(siloxanes) or silicones for insulating ability; poly(methyl methacrylate) for physical strength and transparency; poly(vinyl alcohol) for hydrophilicity and strength; poly(ethylene) for toughness and lack of swelling; poly(vinyl pyrrolidone) for suspension capabilities, etc. Several polymers (such as poly(2-hydroxyethyl-methacrylate); poly(N-vinyl pyrrolidone); poly(vinyl alcohol); poly(acrylic acid); polyacrylamide; poly(ethylene-co-vinyl acetate); poly(ethylene glycol); poly(methacrylic acid), etc.) are utilized for controlled drug delivery. Certain polymers (such as polylactides, polyglycolides, poly(lactide-co-glycolides), polyanhydrides, and polyorthoesters) degrade within a biological tissue, or in a biological subject's body. For example, in an embodiment, one or more polymers are inter-mixed with the resin, or is included as a part or all of the housing for the resin.

Other polymers suitable for use with the resin or housing include, among others, polyester, polylactic acid, polylactic-co-glycolic acid, cellulose, nitrocellulose, urea, urethane, phosphatidylcholine, cholesterol, phosphatidylethanolamine, phospholipid, ganglioside, dioleoylphosphatidylethanolamine, surfactant, polyacid, phthalate, chitin, chitosan, collagen, polyethylene oxide, poly (β-benzyl-L-aspartate), poly (ε-caprolactone), poly(DL-lactide-co-glycolide), polybutylcyanoacrylate, gelatin, 1,5-dioxepan-2-one, D,L-dilactide, alginate, poly(adipic anhydride) or other polymer. In an embodiment, the polymer includes, among others, polyvinyl acetate phthalate, hydroxypropyl methyl cellulose phthalate, methacrylic acid-methacrylic acid ester copolymers, cellulose acetate trimellitate, carboxymethyl ethylcellulose, hydroxypropyl methylcellulose acetate succinate, cellulose acetate phthalate, or other polymer.

In an embodiment, the biological subject includes at least one vertebrate or invertebrate animal. In an embodiment, the biological subject includes a plant (e.g., the ingestible salt grabber is ingested by the plant via uptake from the roots, or transfer to xylum or phloem). For example, in soil that contains a particular high level of an ion (e.g., contaminated soil) such compositions assist in removing toxicity from soil and speed clean up of the site.

In an embodiment, acidic or basic hydrogels respond to particular changes in pH (for example, by swelling). In an embodiment, ionic hydrogels respond to a change in ionic strength (for example by swelling).

In at least one embodiment, the at least one biological tissue is at least partially located in a biological subject. In an embodiment, as discussed herein, a biological subject includes, but is not limited to, a vertebrate or invertebrate, including a fish, reptile, mammal, amphibian, or bird. In at least one embodiment, the biological subject includes at least one human. In an embodiment, the at least one biological subject includes at least one of livestock, pet, zoo animal, undomesticated herd animal, wild animal, aquatic plant or animal, or product animal.

In an embodiment, the at least one biological subject includes at least one of a sheep, goat, frog, dog, cat, rat, mouse, vermin, monkey, horse, cow, pig, chicken, shellfish, fish, turkey, llama, alpaca, bison, buffalo, ape, primate, ferret, wolf, fox, coyote, deer, rabbit, guinea pig, yak, chinchilla, mink, reindeer, elk, camel, fox, elk, deer, raccoon, donkey, or mule. In an embodiment, the at least one biological subject includes at least one anthozoan species. In an embodiment, the at least one biological subject includes at least one of a sea anemone, coral, mollusk, fish, whale, dolphin, porpoise, seal, otter, beaver, seabird, gull, pelican, albatross, duck, swan; or goose. In an embodiment, the at least one subject includes at least one insect (e.g., fly, mosquito, beetle, moth, butterfly, etc.). In an embodiment, the at least one biological subject includes at least one arachnid. In an embodiment, the at least one biological subject includes at least one crustacean.

In an embodiment, the biological subject includes a plant. In an embodiment, the at least one biological tissue includes one or more of a stalk, stem, leaf, root, plant, or tendril. In an embodiment, the at least one biological tissue includes at least one food product. In an embodiment, the at least one food product includes one or more animal, plant, fungal or other biological food product. In an embodiment, the food product includes meat. In an embodiment, the at least one biological tissue includes at least one cell mass or wound.

In an embodiment, the at least one composition is self-administered by the at least one subject. In an embodiment, the at least one composition is ingested by the at least one subject. In an embodiment, the at least one biological tissue includes at least one implantable or transplantable biological tissue. In an embodiment, the at least one biological tissue is transplanted or implanted into at least one subject. In an embodiment, the at least one biological tissue is from at least one donor or recipient. In an embodiment, the at least one biological tissue includes at least one bodily orifice of a subject.

In an embodiment, at least one component of the composition is biodegradable. In an embodiment, hydrogels containing electron-accepting groups respond to electron-donating compounds by forming charge/transfer complexes (for example, by swelling). In an embodiment, hydrogels containing immobilized enzymes respond to particular substrates, such as enzyme conversion (for example, by swelling). In an embodiment, ferrogels respond to magnetic fields by swelling (as a result of changes in pore size of the gel). In an embodiment, thermoresponsive hydrogels (e.g., poly (N-isopropylacrylamide) respond to changes in temperature by changes in polymer-polymer and water-polymer interactions (for example, by swelling). In an embodiment, a polyelectrolyte hydrogel responds to an applied electric field, such as with membrane charging or electrophoresis of charged therapeutics contained therein, by releasing the therapeutic. In an embodiment, ethylene-vinyl alcohol hydrogels respond to ultrasound irradiation and temperature increase by release of the therapeutic agent contained therein.

For many polymers, the response to stimuli (for example, swelling) are reversible and repeatable upon additional changes in the external environment. Certain biodegradable polymers are designed to degrade as a result of hydrolysis of the polymer chains into biologically acceptable, and progressively smaller, compounds. For example, with polylactides, polyglycolides, and their copolymers, the polymers will eventually break down to lactic acid and glycolic acid, which then enter the Kreb's cycle (in vertebrates), and are further broken down into carbon dioxide and water. Degradation can occur through bulk hydrolysis, in which the polymer degrades in a fairly uniform manner throughout the matrix, or (for example, with polyanhydrides and polyorthoesters) the degradation occurs only at the surface of the polymer, resulting in a release rate that is proportional to the surface area of the polymer exposed.

In the case of ferrogels, typically micron sized magnetic particles of $Fe_3O_4$ are dispersed in a polyvinyl alcohol (PVA) hydrogel. The multiferroic ferrogel combines the elastic properties of PVA gel and the magnetic properties of iron. The ferrogel contorts based on application of magnetic field, and can be controlled by the $Fe_3O_4$ concentration and magnetic field strength. Thus, such ferrogel systems are useful for "on-off" type transducers (for example, for the one or more controllable ports). See, for example, Ramanujan and Lao, Smart Mat. Struct.; Vol. 15, pp. 952-956 (2006), which is incorporated herein by reference.

In an embodiment, the composition is coated, for example, with at least one of dextran sulfate, casein, whey protein, or saccharide.

In an embodiment, the resin is in the form of at leak one of beads, powder, or fiber. In an embodiment, the resin is in the form of particles having a diameter of at least about 1 nm, at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 150 nm, at least about 200 nm, at least about 300 nm, at least about 400 nm, at least about 500 nm, at least about 600 nm, at least about 700 nm, at least about 800 nm, at least about 900 nm, at least about 1 μm, at least about 10 μm, at least about 20 μm, at least about 30 μm, at least about 40 μm, at least about 50 μm, at least about 60 μm, at least about 70 μm, at least about 80 μm, at least about 90 μm, at least about 1 mm, at least about 5 mm, at least about 10 mm, at least about 20 mm, at least about 30 mm, at least about 40 mm, at least about 50 mm, at least about 100 mm, or any value therebetween or greater.

In an embodiment, the resin suitable for removing at least one ion (e.g., sodium, potassium, calcium, etc.) are present in aqueous solution at a concentration of at least about 10 ppm, at least about 20 ppm, at least about 30 ppm, at least about 40 ppm, at least about 50 ppm, at least about 60 ppm, at least about 70 ppm, at least about 80 ppm, at least about 90 ppm, at least about 100 ppm, at least about 150 ppm, at least about 200 ppm, at least about 250 ppm, at least about 300 ppm, at least about 350 ppm, at least about 400 ppm, at least about 450 ppm, at least about 500 ppm, at least about 550 ppm, at least about 600 ppm, at least about 650 ppm, at least about 700 ppm, at least about 750 ppm, at least about 8000 ppm, at least about 850 ppm, at least about 900 ppm, at least about 950 ppm, at least about 1000 ppm, at least about 1100 ppm, at least about 1200 ppm, at least about 1300 ppm, at least about 1400 ppm, at least about 1500 ppm, at least about 1600 ppm, at least about 1700 ppm, at least about 1800 ppm, at least about 1900 ppm, at least about 2000 ppm, at least about 2100 ppm, at least about 2200 ppm, at least about 2300 ppm, at least about 2400 ppm, at least about 2500 ppm, at least about 2600 ppm, at least about 2700 ppm, at least about 2800 ppm, at least about 2900 ppm, at least about 3000 ppm, at least about 3100 pm, at least about 3200 ppm, at least about 3300 ppm, at least about 3400 ppm, at least about 3500 ppm, at least about 3600 ppm, at least about 3700 ppm, at least about 3800 ppm, at least about 3900 ppm, at least about 4000 ppm, or any value therebetween or greater.

In an embodiment, the resin is suitable for use with an aqueous solution having a pH at about 1, at about 2, at about 3, at about 4, at about 5, at about 6, at about 7, at about 8, at about 9, at about 10, or any value therebetween.

In an embodiment, the porosity of the resin includes pores of about 0 to about 500 Å in diameter; or about 0 to about 500 m²/g.

In an embodiment, for example, a resin (R) has a greater affinity for ion B than for ion A. If the resin contains ion A and ion B is dissolved in the water or other aqueous fluid passing through it, then the ion exchange reaction occurs (proceeding to the right):

$$AR + B^{n+/-} \leftrightarrow BR + A^{n+/-}$$

In an embodiment, a resin in an environment with pH values above at least 3.5, allows divalent ions (e.g., calcium) to enter the resin in amounts greater than those characteristic of monovalent ions. In an embodiment, among monovalent ions, however, there may be variable affinity of the resin for the various positively charged ions (e.g., dependent on the atomic weight, valence, size of the ion, etc.) and can be modified by the degree of resin swelling, nature of the housing, nature of the solvent, pH of the suspension, and the concentrations of the various ions competing for a position on the resin. See, for example, Friedman et al.; Arch. Intern Med.; Vol. 89 (1), pp. 99-106 (1952), which is incorporated herein by reference.

Methods of making the disclosed resin compositions may be conducted in a particular sequence, depending on the components of the composition, or the desired qualities of the composition. For example, in an embodiment a coating includes a crosslinked polymer. In certain instances, the polymer is crosslinked during the polymerization reaction, and in other instances the monomer(s) are polymerized and then the resulting polymer is subsequently treated with a crosslinking agent to form the crosslinked polymer. Likewise, in an embodiment, the polymer coating is prepared prior to combining with the internal resin. In an embodiment, the uncrosslinked polymer is coated on the resin prior to the coating being treated with the crosslinking agent to form the crosslinked polymer.

As described herein, in an embodiment the housing includes at least one polymeric coating. In an embodiment, the compositions disclosed herein further include at least one enteric coating or binding materials to reduce reactivity with the resin at the low pH of the stomach, and instead allow for highest reactivity to occur in the intestinal tract.

As described herein, in an embodiment the housing is configured to regulate access of ion solutes to the internal resin. For example, in an embodiment, the permeability of the housing to divalent cations decreases by reducing the porosity of the housing. In an embodiment, incorporating positive charges into the housing that create electrostatic repulsion with the multivalent cations also reduces access to the resin. In an embodiment, a target ion is desired to be bound to the composition, and a competing ion is an ion that competes with the target ion for the binding capacity of the resin. In an embodiment, the resin includes binding characteristics or permeability characteristics that favor the target ion(s). In an embodiment, a competing ion is prevented from contacting or binding the resin due to at least one of preferential binding characteristics of the resin, decreased permeability of the housing for the competing ion, or other factors. In an embodiment, the housing is permeable to both monovalen and divalent cations. In an embodiment, the housing is permeable to only one of monovalent or divalent cations, but not both. In an embodiment, the housing has a reduced permeability to higher valency cations (e.g., by changing the porosity, average pore size, charge density, or hydrophobicity of the housing, etc.). For example, magnesium and calcium hydrated ions are larger in size compared with monovalent cations such as potassium and sodium. See U.S. Pat. No. 7,556,799, which is incorporated herein by reference.

In an embodiment, the hydrophobicity of the resin causes a reduced interaction with particular cations, and can be altered depending on the target ion(s) and competing ion(s). In an embodiment, the resin has polymers embedded within it that can swell and decrease access to the resin itself (thereby limiting access for binding), which can be regulated by pH, hydrophobicity, crosslinking density, charge density, or solvent ionic strength. In an embodiment, the pH regulates the access or binding of ions to the resin. For example, the binding capacity of the resin can be adjusted such that it has a low binding capacity at gastric pH (e.g., about 3.5, or lower), and a higher binding capacity at the pH of the intestinal tract (e.g., about 5 or higher).

In an embodiment, the access or binding capacity of the resin or coating is further regulated by residence time in the gastro-intestinal tract. For example, in an embodiment, the composition(s) disclosed herein include one or more cell surface molecules (e.g., adhesion molecules) that are formulated to bind to one or more cells in the gastro-intestinal tract during transit through the gut, and extend the residence time (thus, allowing for temporal regulation of uptake of the target ion(s) or allowing for additional uptake of ion(s)).

In an embodiment, at least one of the housing or the resin is permeable or has another selectivity mode through passive absorption while passing through at least part of the gastro-intestinal tract. For example, many soluble materials are charged and are hydrophobic (e.g., due to fatty acid composition, amino acid composition, or other components). In an embodiment, the selectivity of at least one of the housing or the resin is modulated by at least one enzyme of the gastro-intestinal tract. For example, enzymes such as collagenase, neuraminidase, deoxyribonuclease, heparinase, proteinase, lipase, and other enzymes are found in various locations along the gastro-intestinal tract. In an embodiment, at least one enzyme modulates the selectivity of the housing or resin by, for example, cleaving hydrophilic moieties from the hydrophobic backbone of at least one component of the composition.

In an embodiment, the housing is joined to the resin (e.g., physically, chemically, magnetically, electrically, etc.).

In an embodiment, a method of modulating at least one ion in a biological tissue, comprises providing a composition to a biological tissue, the composition including a housing including at least one ingestible resin and one or more controllable ports. In an embodiment, the at least one ingestible resin includes at least one of an anion exchange resin or cation exchange resin. In an embodiment, the biological tissue is located in a biological subject. In an embodiment, the biological subject is a vertebrate or invertebrate. In an embodiment, the biological subject is a plant. In an embodiment, the method further comprises monitoring at least one ion in a biological sample prior to, during, or subsequent to providing the composition including at least in ingestible resin and one or more controllable ports to the biological tissue. In an embodiment, the biological sample includes at least one biological tissue or biological fluid. In an embodiment, the at least one ion includes at least one of wherein the one or more ions include at least one of sodium, potassium, ammonium, magnesium, iron, lithium, or calcium.

In an embodiment, a method of modulating at least one ion in a biological tissue, comprises providing a composition to a biological tissue, the composition including at least one ingestible resin and one or more cell surface molecules. In an embodiment, the biological tissue is located in a biological subject.

In an embodiment, a foodstuff, comprises an ingestible food product including at least one ion exchange resin. For example, in an embodiment, the ingestible food product includes at least one of plant or animal matter. In an embodiment, the ingestible food product includes at least one processed food product. In an embodiment, the ingestible food product includes at least one of milk, soup, dairy products, grain products, fruit products, or vegetable products. In an embodiment, the ingestible food product includes a beverage (e.g., water, milk, soft drinks, juice, etc.). In an embodiment, the ingestible food product includes animal feed (e.g., grain, etc.).

In an embodiment, an article of manufacture comprises an article including a composition having an ingestible resin and one or more cell surface molecules. In an embodiment, an article of manufacture comprises an article including a composition having a housing with one or more controllable ports, and at least one ingestible resin. In an embodiment, the article includes at least one of gum, pacifier; food dish or food dish cover; condiment container, utensil or utensil cover, dental implant; dental accessory; or paper product. In an embodiment, the paper product includes at least one paper packet. In an embodiment, the condiment container is in the form of a condiment packet. In an embodiment, the condiment container is in the form of a condiment bottle. In an embodiment, the condiment container includes at least one of a salt or pepper container. In an embodiment, the article is at least one of reusable or disposable. In an embodiment, the article is configured to maintain the composition in an anhydrous form. In an embodiment, the article includes multiple different ingestible resins.

Figure 1:
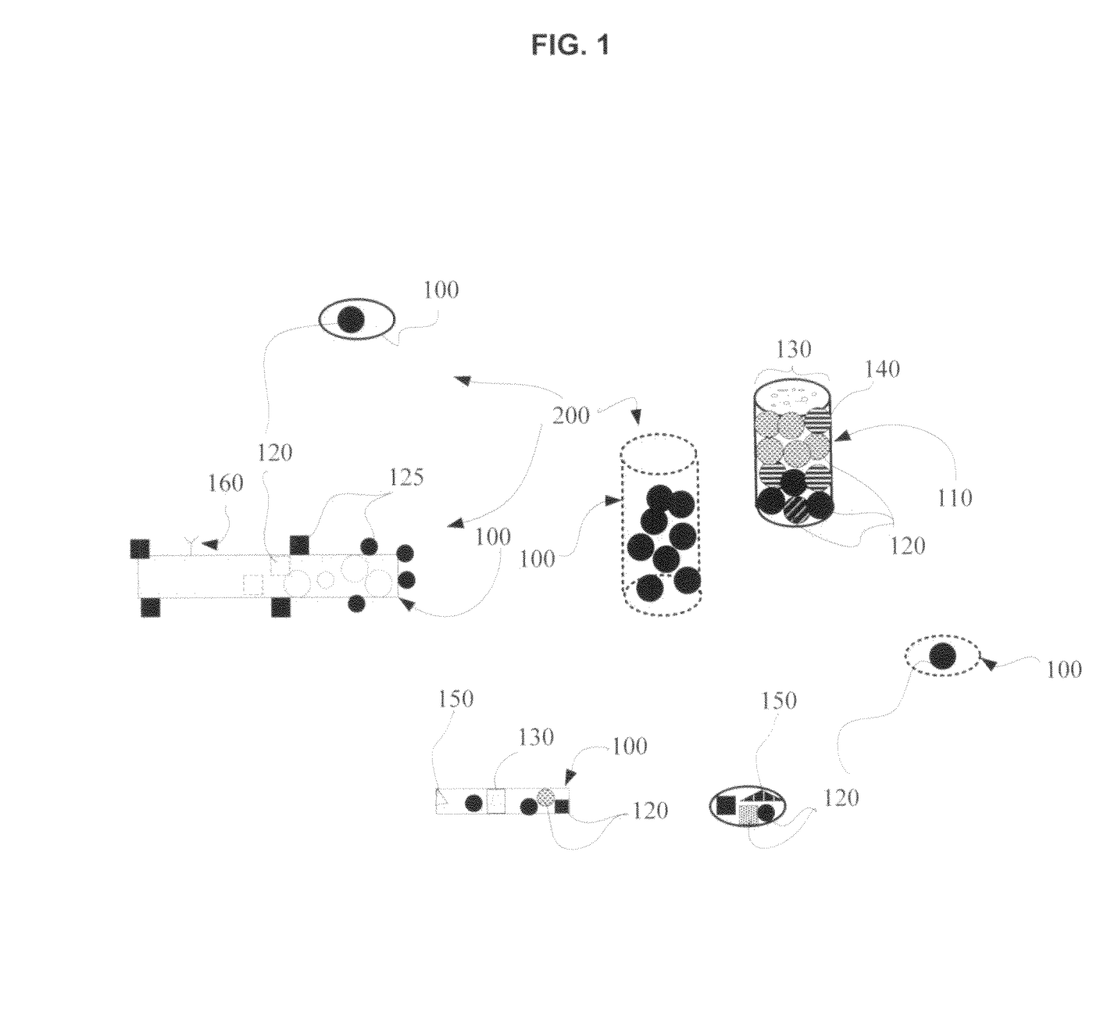
FIG. 1 illustrates various embodiments of compositions disclosed herein.

As indicated in the FIG. 1, in an embodiment, a composition 200 includes a housing 100, including at least one ingestible resin 120, and one or more controllable ports 130. In an embodiment, the housing 100 is in the form of a container 110 (e.g., condiment container that also contains one or more ions 140, which in certain instances, include one or more target ions). As illustrated in FIG. 1, in an embodiment, a container 110 includes one or more controllable ports by which the resin is able to be accessed (e.g., by shaking onto a foodstuff and then ingested by a biological subject). In an embodiment, the composition 200 includes one or more resins 125 external to the housing 100. In an embodiment, the composition 200 includes one or more cell surface molecules 160 (e.g., an adhesion molecule or antibody or portion thereof). In an embodiment, the one or more cell surface molecules 160 are located external to the housing 100. In an embodiment, the one or more cell surface molecules 160 are located internal to the housing 100. In an embodiment, the composition includes at least one sensor 150.

Figure 2:
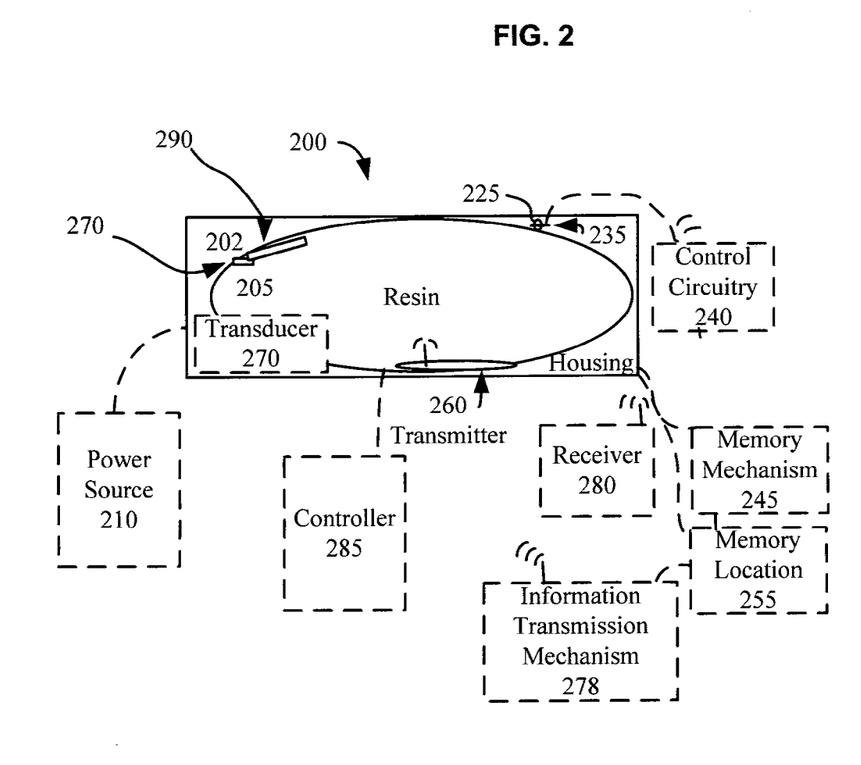
FIG. 2 illustrates various embodiments of compositions disclosed herein.

As indicated in FIG. 2, in an embodiment, a composition 200, includes a housing 202 including at least one resin 205. In an embodiment, the composition includes one or more controllable ports 225. In an embodiment, at least one controllable output mechanism 235 is operably linked to the one or more controllable ports 225 to control dispensing of at least a portion of the at least one composition 200.

In an embodiment, the composition further comprises at least one control circuitry 240 configured to generate and transmit an electromagnetic control signal configured to control the at least one controllable output mechanism 235. In an embodiment, the composition further comprises a transducer 270. In an embodiment, the composition further comprises a transmitter 260. In an embodiment, the composition 200 further comprises a receiver 280. In an embodiment, the composition 200 further comprises a power source 210.

In an embodiment, the composition 200 further comprises at least one detection material 290. In an embodiment, the detection material 290 includes at least one of a taggant, contrast agent, sensor 270, or electronic identification device. In an embodiment, the delivery device further comprises a controller 285 configured to respond to the at least one sensor 270. In an embodiment, the composition 200 further comprises a memory mechanism 245 for storing instructions for generating and transmitting an electromagnetic control signal. In an embodiment, the composition 200 further comprises at least one memory location 255 for recording information. In an embodiment, the composition further comprises an information transmission mechanism 278 configured to transmit information recorded by the at least one electronic memory location.

The following Examples are intended to be illustrative of various embodiments, and are non-limiting in any way.

PROPHETIC EXAMPLES

Example 1

Enclosed Compositions Including Controlled Ports Containing an Ion Exchange Resin to Sequester Sodium Ions Until They are Eliminated by Excretion A subject with vascular hypertension is advised to reduce his uptake of sodium ions. The subject adds enclosed compositions containing a cation exchange resin to his food prior to eating. After ingestion the enclosed compositions traverse the gastrointestinal tract until they bind to mucosal receptors in the small intestine where controlled ports selectively allow sodium ions, present in the intestinal fluid, to reach and bind the cation exchange resin inside the enclosed compositions. The enclosed compositions with bound sodium ions are retained in the small intestine until their ion exchange resin is saturated with sodium ions and they are released and excreted.

Enclosed compositions are constructed with reservoirs, ion exchange resins, ion selective membranes and surface molecules that adhere to the mucosa of the small intestine. They are fabricated from silicon dioxide wafers (p-type) using photolithography, etching, and deposition to contain reservoirs that are capped with a sodium ion selective membrane. Enclosed compositions with a thickness of approximately 0.2-0.5 mm and lengths and widths of approximately 1.0-3.0 mm are fabricated with reservoirs that hold approximately 0.50 µl of liquid.

Particular aspects of specific methods to fabricate controlled release compositions with reservoirs are described. See e.g., Ahmed et al., *Journal of Controlled Release* 81: 291-306, 2002, which is incorporated herein by reference. Similarly, sequential steps of low pressure chemical vapor deposition may be used to layer poly-silicon and low temperature oxide on a silicon wafer for the enclosed compositions of the present disclosure. Next, reservoirs are created by positive photolithography and reactive ion etching. The reservoirs are then filled with a sodium polystyrene sulfonate strong acid cation exchange resin (See e.g., Product Data Sheet for Purolite C100NaMR available from The Purolite Company, Bala Cynwyd, Pa.; which is included herein by reference). The cation exchange resin is then treated with 4 N HCl to obtain the H$^+$ form of the resin and then a microinjection apparatus is used to fill the reservoirs with approximately 0.5 mg of resin particles (See e.g., Ahmed et al., *Ibid*. for microinjection methods).

The enclosed composition reservoirs are capped with a membrane containing a sodium ion ionophore to enclose the ion exchange resin and to provide controlled ports that selectively allow sodium ions access to the reservoir. For example a sodium selective membrane is made with sodium ionophore, X (tert-butylcalix[4]arene tetraethyl ester)(10 mmol/kg), polyvinyl chloride (33 wt %), bis(2-ethylhexyl) sebacate (DOS) (66 wt %), and sodium tetrakis [3.5bis(trifluoromethyl)phenyl] borate (NaTFPB)(0.3 mmol/kg) dissolved in cyclohexanone and dichloromethane. All chemicals are available from Fluka, Milwaukee, Wis. The ionophore/polymer solution may be spin coated onto the enclosed compositions and the solvent is evaporated at room temperature. Methods to make ion selective membranes are described. See e.g., U.S. Pat. No. 7,651,858, which is incorporated herein by reference. The enclosed compositions are targeted to the small intestine by conjugating a protein, tomato lectin (*Lycopersicon esculentum*), which binds carbohydrate moieties present in the mucosa lining the small intestine. The enclosed compositions are treated with HCl and $H_2O_2$ to make them hydrophilic, and then silanized prior to conjugating tomato plant lectin to the surfaces of the enclosed compositions. Methods to conjugate tomato plant lectin (available from Sigma-Aldrich, St. Louis, Mo.) to the silicon surface have been published. See e.g., Ahmed et al., *Ibid.*

In order to reduce salt uptake, the subject ingests enclosed compositions containing ion exchange resins behind a sodium selective membrane. Ordinary diets provide an average daily intake of approximately 100 to 300 meq of sodium, and to reduce sodium uptake the subject may require approximately 5 gm to 50 gm of a cation ion exchange resin (see e.g., Greenman et al., *J. Clin. Invest.* 30: 1027-1031, 1951, and Spencer et al., *Brit. Med.* 11: 603-606, 1954, each of which are incorporated herein by reference). Each enclosed composition contains approximately 0.5 mg of ion exchange resin, and thus approximately $10^4$ to $10^5$ enclosed compositions are required. The enclosed compositions containing ion exchange resin may be taken daily for intervals of approximately 3 to 12 days (see e.g., Danowski et al., *Ann. Internal Med.* 35: 529-541, 1951, which is incorporated herein by reference). The ingested enclosed compositions pass through the stomach and adhere to the mucosa of the small intestine by binding N-acetylglucosamine moieties through tomato lectin which is immobilized on the surface of the enclosed compositions. The enclosed compositions remain in the small intestine and sequester sodium ions that pass from the intestinal fluids through the sodium ion selective membrane and bind the ion exchange resin. The enclosed compositions are left in the small intestine for approximately 3-12 days or until the ion exchange resin has bound the maximum amount of sodium ion (see e.g., Spencer et al., *Ibid.*). The enclosed compositions may be released from the small intestine by ingestion of N-acetylglucosamine which competes with intestinal mucosa for binding to tomato lectin immobilized on the enclosed compositions. N-acetylglucosamine is available as a Chitin Hydrolysate from Vector Labs, Inc., Burlingame, Calif. (See e.g., Vector Labs Product Data Sheet: Chitin Hydrolysate which is incorporated herein by reference). The subject is monitored with respect to his blood pressure, plasma sodium ion concentration and stool sodium ion concentration. Assays for these parameters are described, for example, in Spencer et al., *Ibid.*

Example 2

An Ingestible Enclosed Composition with Controllable Ports Containing an Ion Exchange Resin A subject with congestive heart failure is advised to control his intake of sodium ions. The subject controls salt consumption by limiting salt in his diet and by adding enclosed compositions containing ion exchange resin to his food. The enclosed compositions have ports controlled remotely by an alternating magnetic field (AMF) and they are closed once sodium ions have been sequestered by the ion exchange resin within the enclosed compositions. The sequestered sodium ions are retained in the enclosed composition and excreted via the bowels. Once the enclosed compositions are ingested, the controllable ports can be opened by externally applying an AMF to the small intestine or other sites in the gastrointestinal tract.

Enclosed compositions containing ion exchange resins are constructed to selectively sequester sodium ions and eliminate them when the enclosed compositions are excreted. Enclosed compositions are constructed with reservoirs, ion exchange resins, and controllable ports. The enclosed compositions are fabricated from silicon dioxide wafers (p-type) using photolithography, etching, and deposition to contain reservoirs that are capped with a membrane containing controllable pores. Enclosed compositions with a thickness of approximately 0.2-0.5 mm, and lengths and widths of approximately 1.0-3.0 mm, are fabricated with reservoirs that hold approximately 0.50 μl of liquid. Particular aspects of a specific method to fabricate controlled release compositions with reservoirs are described. See e.g., Ahmed et al., *Journal of Controlled Release* 81: 291-306, 2002 and U.S. Pat. No. 6,123,861, each of which is incorporated herein by reference.

For example, the enclosed compositions of the instant disclosure are made by sequential steps of low pressure chemical vapor deposition used to layer poly-silicon and low temperature oxide on a silicon wafer. Next, reservoirs are created by positive photolithography and reactive ion etching. Next, the reservoirs are filled with a sodium polystyrene sulfonate strong acid cation exchange resin. (See e.g., Product Data Sheet: "Purolite C100NaMR" available from The Purolite Company, Bala Cynwyd, Pa.; which is included herein by reference). The cation exchange resin is treated with 4 N HCl to obtain the $H^+$ form of the resin, and then a microinjection apparatus is used to fill the reservoirs with approximately 0.5 mg of resin particles (See e.g., Ahmed et al., *Ibid.* for microinjection methods).

The enclosed composition reservoirs are capped with a thermoswitchable polymer membrane that responds to temperature changes by closing the ports present in the polymer membrane. Thermoswitchable polymer membranes that respond to temperature have been published (see e.g., International Publication No. WO2008/012725, which is incorporated herein by reference). Thermoswitchable polymers exhibit a critical solution temperature. The critical solution temperature is the temperature at which the polymer displays a phase transition from an extended and soluble conformation to a globular collapsed and insoluble conformation. In the extended conformation, the polymer chains are fully solvated, leaving an open and permeable structure, whereas in the collapsed state the polymer structure becomes relatively impermeable. Thermoswitchable polymers include poly-N-isopropylamide (poly-PNIPAAm) and copolymers thereof, polyoxyethylene trimethylol-propane distearate and poly-E-caprolactone. The critical solution temperature may be determined by measuring the polymer volume as a function of temperature. Polymers that display a phase transition upon a decrease of the temperature exhibit an upper critical solution temperature (UCST).

For example, a copolymer of N-isopropylamide and acrylamide exhibits a phase transition from an extended conformation to a collapsed insoluble conformation when the temperature falls below the upper critical solution temperature (UCST). The polymer mesh size and phase transition temperature response can be tailored by adjusting the composition of the monomer, comonomer, and crosslinkers. For example incorporating a hydrophilic comonomer like acrylamide can alter the critical solution temperature. A polymer membrane with an ucst equal to approximately 42° C. is used to cap the enclosed composition reservoirs and to provide controllable ports that restrict solvent access to the ion exchange resin contained in the reservoirs. The controlled ports in the polymer membrane will be closed at normal body temperature, approximately 37° C. and opened when the polymer membrane is heated to 42° C.

To allow remote control of the temperature of the thermoswitchable polymer membranes, they are constructed with superparamagnetic $Fe_3O_4$ nanoparticles that generate heat when a high frequency alternating magnetic field (AMF) is applied. Methods and materials to construct thermoswitchable polymers containing $Fe_3O_4$ nanoparticles are described. See e.g., Satarkar and Hilt, *J. Control. Rel.* 130: 246-251, 2008, which is incorporated herein by reference. For example, polymers may be synthesized with NIPPAAm as monomer and Tetra (ethyleneglycol) dimethacrylate (TEGDMA) as crosslinker by redox polymerization (chemicals available at Polysciences, Inc., Warrington, Pa.). $Fe_3O_4$ nanoparticles, approximately 5% (wt/wt) (available from Nanostructured and Amorphous Materials Inc., Houston, Tex.) are added to the NIPPAAm and TEGDMA polymer components and dispersed by sonication. Thermoswitchable polymer membranes containing 5% $Fe_3O_4$ are heated by application of an AMF of 5.3 kA/m (strength) and 297 kHz (frequency) to their critical solution temperature and a phase transition. Increasing the percentage of $Fe_3O_4$ nanoparticles in the membranes increases the amount of heat produced following application of an AMF.

The subject ingests enclosed compositions containing ion exchange resin with his food, prior to meal time, or subsequent to meal time. Approximately 5,000 enclosed compositions are ingested to provide approximately 5 grams of ion exchange resin. The enclosed compositions have reservoirs capped with a thermoswitchable polymer membrane containing $Fe_3O_4$ that allows heating of the caps by applying high frequency AMF. The polymer membrane caps have an upper critical solution temperature of 42° C. When the caps are at less than 42° C. the polymer is collapsed and impermeable with ports closed. This corresponds to normal body temperature, 37° C.

Approximately 2-3 hours after ingestion of the enclosed compositions the patient's abdominal region is exposed to an AMF that heats the Fe3O4 nanoparticles to approximately 42° C. and results in opening of the ports on the caps to allow intestinal fluid, including sodium ions, access to the reservoirs and the ion exchange resin. The AMF is applied for approximately 30 minutes to allow sodium ions to enter the reservoir and bind the ion exchange resin. Next, the AMF field is removed, and the ports close leaving reservoirs filled with sodium ions that are excreted along with the enclosed compositions.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A composition, comprising:
   a housing with at least one electronic identification device;
   the housing containing at least one ingestible ion exchange resin, and one or more thermoswitchable membrane controllable ports with supraparamagnetic iron oxide nanoparticles embedded therein and configured to heat upon exposure of an alternating magnetic field.

2. The composition of claim 1, wherein the at least one housing further includes at least one coating.

3. The composition of claim 2, wherein the at least one housing includes at least one of a permeable coating, or a semi-permeable coating.

4. The composition of claim 3, wherein the at least one housing is semi-permeable for one or more ions.

5. The composition of claim 4, wherein the one or more ions include at least one of sodium, potassium, ammonium, magnesium, iron, lithium, or calcium.

6. The composition of claim 4, wherein the at least one housing is semi-permeable for sodium.

7. The composition of claim 3, wherein the at least one housing is semi-permeable based at least in part on size exclusion.

8. The composition of claim 3, wherein the at least one housing is semi-permeable for one or more locations of a gastro-intestinal tract.

9. The composition of claim 3, wherein the one or more controllable ports are configured to be regulated by at least one of pH, ion level, temperature, light, magnetic field, electrical field, or chemical concentration.

10. The composition of claim 2, wherein the housing is biodegradable and configured to degrade or increase in permeability based at least in part on one or more of external command, schedule, location, or response to one or more sensors.

11. The composition of claim 2, wherein the housing includes at least one of a carbohydrate, protein, or lipid.

12. The composition of claim 2, wherein the housing includes a starch.

13. The composition of claim 2, wherein the housing includes at least one polymer.

14. The composition of claim 1, wherein the resin is configured to selectively bind at least one of sodium, potassium, ammonium, magnesium, iron, lithium, calcium, or phosphates thereof.

15. The composition of claim 1, wherein the porosity of the at least one ingestible resin includes pores of about 0 to about 500 Angstroms in diameter or any value therebetween.

16. The composition of claim 1, wherein the affinity of the at last one ingestible resin for a particular ion is configured to change depending on the location in the gastro-intestinal tract.

17. The composition of claim 1, wherein the affinity of the at least one ingestible resin for a particular ion is configured to change depending on at least one of pH, ion level, temperature, light, or chemical concentration.

18. The composition of claim 1, wherein the affinity of the at least one ingestible resin for a particular ion is configured to change depending on the type of other ions present.

19. The composition of claim 1, wherein the one or more controllable ports are configured to be controlled to at least one of open, close, or modulate permeability of the at least one housing.

20. The composition of claim 1, wherein the one or more controllable ports are configured to be controlled based in part on at least one of external command, schedule, location, or response to one or more sensors.

21. The composition of claim 20, wherein the one or more sensors are configured to detect at least one of pH, ion level, temperature, light, or chemical concentration.

22. The composition of claim 1, wherein the composition includes at least one surface molecule configured to adhere to at least one location of a gastro-intestinal tract.

23. The composition of claim 1, wherein the composition is formulated to be ingested just prior to, during, or just subsequent to food intake.

24. The composition of claim 1, wherein the composition is formulated to be ingested by a subject.

25. The composition of claim 1, wherein the ion exchange resin includes an anion exchange resin.

26. The composition of claim 1, wherein the ion exchange resin includes a cation exchange resin.

27. The composition of claim 1, wherein the at least one ion exchange resin includes at least two ion exchange resins.

28. The composition of claim 27, wherein the at least one ion exchange resin includes at least one of each an anion exchange resin and a cation exchange resin.

29. The composition of claim 1, wherein the housing includes at least a portion of a microchip or nanochip.

30. The composition of claim 1, wherein the at least one ingestible resin is in the form of at least one of bead, powder, or fiber.

31. The composition of claim 1, further including at least one pharmaceutical vehicle or excipient.

32. The composition of claim 1, wherein the at least one ingestible resin includes at least one silicate.

33. The composition of claim 32, wherein the at least one ingestible resin includes zeolite.

34. The composition of claim 1, wherein the housing is at least one of biodegradable, biocompatible, or non-toxic.

35. The composition of claim 1, wherein the one or more controllable ports include at least one hydrogel.

36. The composition of claim 35, wherein the hydrogel includes at least one ferrogel.

37. The composition of claim 1, wherein the housing has controllable permeability.

38. The composition of claim 1, wherein the housing includes one or more coatings.

39. The composition of claim 38, wherein at least one of the coatings has higher permeability for a target ion than a competing ion.

40. The composition of claim 1, wherein the housing includes an enclosure containing the at least one ingestible resin.

* * * * *